(12) United States Patent
Farina et al.

(10) Patent No.: US 9,828,334 B2
(45) Date of Patent: Nov. 28, 2017

(54) PROCESS FOR PREPARING LEVOMILNACIPRAN

(71) Applicant: LABORATORIO CHIMICO INTERNAZIONALE S.p.A., Milan (IT)

(72) Inventors: Paolo Maria Farina, Casaletto Lodigiano (IT); René Ignacio Rodriguez Curiel, Alcantarilla (ES); Stefano Maiorana, Milan (IT); Aldo Bianchi, Solaro (IT); Federica Colombo, Milan (IT); Gabriele Timpano, Garbagnate Milanese (IT)

(73) Assignee: OLON S.P.A., Rodano (Milan) (IT)

( * ) Notice: Subject to any disclaimer, the term of this patent is extended or adjusted under 35 U.S.C. 154(b) by 0 days.

(21) Appl. No.: 15/106,024

(22) PCT Filed: Nov. 27, 2014

(86) PCT No.: PCT/IB2014/002586
§ 371 (c)(1),
(2) Date: Jun. 17, 2016

(87) PCT Pub. No.: WO2015/092502
PCT Pub. Date: Jun. 25, 2015

(65) Prior Publication Data
US 2016/0318851 A1 Nov. 3, 2016

(30) Foreign Application Priority Data

Dec. 18, 2013 (IT) ................................ MI2013A2119

(51) Int. Cl.
*C07C 229/00* (2006.01)
*C07C 237/24* (2006.01)
*C07C 271/22* (2006.01)
*C07C 231/20* (2006.01)
*C07C 229/36* (2006.01)

(52) U.S. Cl.
CPC .......... *C07C 237/24* (2013.01); *C07C 229/36* (2013.01); *C07C 231/20* (2013.01); *C07C 271/22* (2013.01); *C07B 2200/07* (2013.01); *C07C 2601/02* (2017.05)

(58) Field of Classification Search
CPC . C07C 231/20; C07C 237/24; C07C 2101/02; C07C 229/36; C07C 271/22; C07B 2200/07
See application file for complete search history.

(56) References Cited

FOREIGN PATENT DOCUMENTS

| WO | WO 2012/059933 | | 5/2012 |
| WO | WO2012059933 | * | 5/2012 |

OTHER PUBLICATIONS

'967 (CN1301967, published Feb. 2007) translation.*
International Search Resort issued in PCT/IB2014/002586 dated Apr. 13, 2015.
Written Opinion of the International Searching Authority issued in PCT/IB2014/002586 dated Apr. 13, 2015.

* cited by examiner

*Primary Examiner* — Yevegeny Valenrod
*Assistant Examiner* — Blaine G Doletski
(74) *Attorney, Agent, or Firm* — Nixon & Vanderhye P.C.

(57) ABSTRACT

The present invention refers to a new process for preparing levomilnacipran, in particular to a process for the resolution of racemic tw-milnacipran with a derivative of optically active phenylglycine.

11 Claims, No Drawings

PROCESS FOR PREPARING LEVOMILNACIPRAN

This application is the U.S. national phase of International Application No. PCT/IB2014/002586 filed Nov. 27, 2014 which designated the U.S. and claims priority to Italian Application No. MI2013A002119 filed Dec. 18, 2013, the entire contents of each of which are hereby incorporated by reference.

SUMMARY OF THE INVENTION

The present invention refers to a new process for preparing levomilnacipran, in particular to a process for the resolution of racemic cis-milnacipran with a derivative of optically active phenylglycine.

BACKGROUND OF THE INVENTION

Levomilnacipran, (1S,2R)-cis-2-(aminomethyl)-N,N-diethyl-1-phenylcyclopropanecarboxamide (also defined (1S,2R)-cis-milnacipran) is a drug actually used in depressive disorders and fibromyalgia, and has the following formula (I)

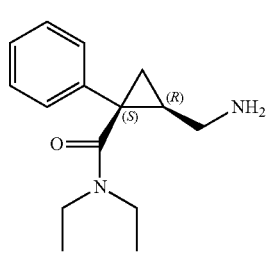

Levomilnacipran is commonly used in the therapy in form of hydrochloride salt. Several synthesis of levomilnacipran are known, most of which consider the resolution of racemic cis-milnacipran by means of resolving agents such as, e.g., optically active derivatives of tartaric acid and mandelic acid.

Such processes, in addition to not providing the desired compound with good yields and acceptable purity, have the disadvantage of a difficult recovery of the resolving agent from the reaction mother liquors; such difficulty represents a problem from the industrial point of view since it is clear that, in the economy of a large scale synthesis, the simple and quantitative recovery of all re-usable reaction agents is fundamental.

OBJECTS OF THE INVENTION

It is an object of the present invention to provide a new industrially favorable synthetic pathway for preparing levomilnacipran.

It is a further object of the present invention to provide a synthetic pathway for preparing levomilnacipran which provides the compound with excellent yields and purity and which allows the simple recovery of re-usable reaction reagents.

DESCRIPTION OF THE INVENTION

Therefore, according to one of its aspects, the invention refers to a process for preparing levomilnacipran ((1S,2R)-cis-milnacipran) of formula (I) by means of resolution of cis-milnacipran with a derivative of optically active phenylglycine.

In particular, the invention refers to a process for preparing levomilnacipran ((1S,2R)-cis-milnacipran) of formula (I)

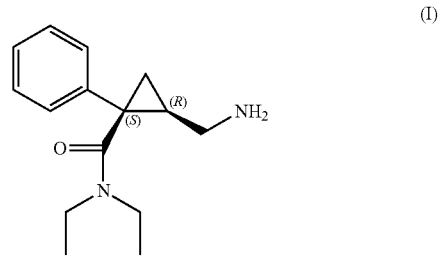

or a salt thereof, comprising
(a) reacting racemic cis-milnacipran free base with a derivative of the optically active L-phenylglycine of formula (II)

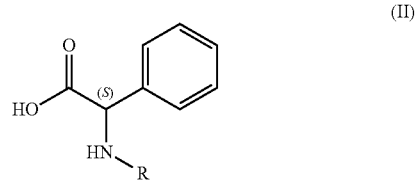

wherein R is an amine protecting group, in a non-aqueous organic solvent, selected preferably from alcohols, ketones and esters to give the salt of formula (III)

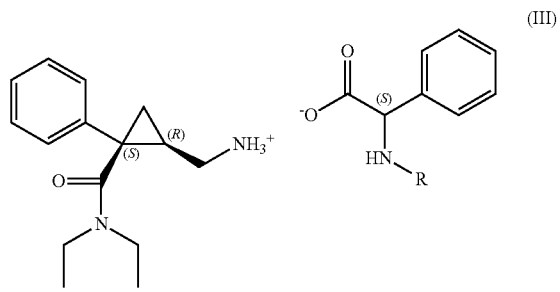

(b) reacting the salt of formula (III) obtained in step (b) with a base, in water, to release levomilnacipran of formula (I);
(c) isolating said levomilnacipran from the reaction mixture of step (b) and purifying it and/or optionally transforming it into a salt of said levomilnacipran.

The racemic cis-milnacipran is a compound well known in the art and is commercially available, generally in the form of hydrochloride salt thereof. The starting racemic cis-milnacipran can be prepared, e.g., from the salt thereof by reacting with a base in water, according to conventional procedures.

According to the present invention, R is preferably a protecting group forming an amide with the amino group of phenylglycine, preferably a group selected from tert-butyloxycarbonyl (Boc), benzoyl and p-methoxybenzylcarbonyl. A preferred compound of formula (II) is N-Boc-L-(+)-phenylglycine.

The reaction of step (a) is advantageously carried out in a solvent selected from alcohols, e.g. lower alcohols, such as ethanol, 2-propanol, butanol, etc; ketones such as, e.g., acetone, isobutyl ketone, methyl ethyl ketone, etc; and esters, such as, e.g., ethyl acetate. Alcohols, in particular 2-propanol, are preferred solvents.

The reaction temperature of step (a) can be comprised between room temperature and the boiling temperature of the reaction mixture, preferably comprised between 50° C. and the boiling temperature of the reaction mixture, even more preferably between 60° C. and 80° C., for example around 70-75° C.

The molar ratio between racemic cis-milnacipran and the compound of formula (II) is preferably substantially equimolar.

The reaction is completed in a short time and, after cooling of the reaction mixture, the salt between levomilnacipran and the compound of formula (II), advantageously the salt between levomilnacipran and N-Boc-L-(+)-phenylglycine, precipitates in the reaction mixture. Then said salt can be isolated, e.g. by filtration, and used for the reaction of the following step. On the other hand the unwanted isomer of cis-milnacipran remains in the mother liquors of the reaction mixture of step (a). Hereafter, the salt of formula (III) between levomilnacipran and the compound of formula (II) is suspended in water in step (b) and by adding a base, for example a hydroxide such as sodium or potassium hydroxide, the levomilnacipran is released from the salt. The reaction mixture is then worked-up according to methods well known to the one skilled in the art for the isolation of the desired compound. By way of example, it is possible to extract the levomilnacipran from the reaction mixture with an organic solvent, e.g. with a chlorinated solvent such as dichloromethane, and to isolate the compound by evaporation of such solvent.

The process of the invention allows to obtain the separation of levomilnacipran from the corresponding racemic compound with quantitative yields and excellent purity. However, if desired or needed, it is possible to further purify the final compound and/or to transform it into a salt thereof, e.g. into the hydrochloride salt thereof, according to conventional procedures.

According to a preferred embodiment of the invention, in step (c) levomilnacipran is transformed into the hydrochloride salt thereof. Advantageously, the salification reaction is carried out in anhydrous environment, e.g. in an organic solvent such as ether, e.g. in methyl-tert-butyl-ether, in presence of an alcohol, e.g. 2-propanol and from hydrogen chloride that can be also generated from a trialkyl-silyl chloride, if needed, e.g. from trimethyl-silyl chloride.

Detailed examples of the process of the invention are provided in the experimental section of the present description.

Salts of formula (III)

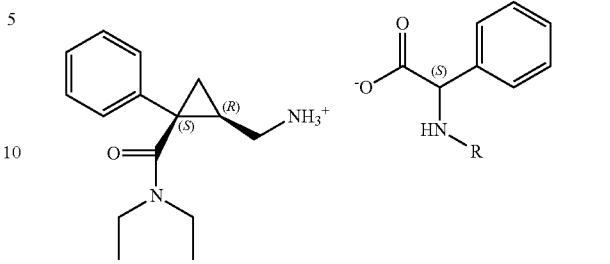

wherein R is a protecting group, are new compounds and represent a further object of the invention.

According to a preferred embodiment of the invention, in compounds of formula (III) R is a protecting group which forms an amide with the amine group of phenylglycine.

A particularly preferred compound of formula (III) is the compound (III')

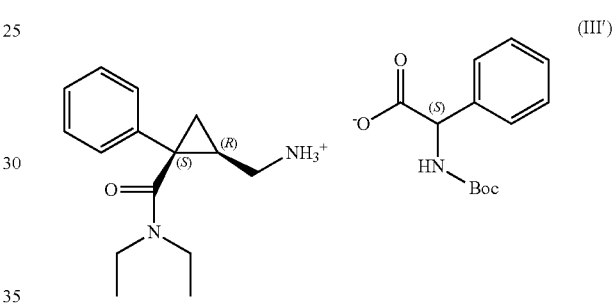

Such (III') compound represents a further preferred object of the invention.

The process of the invention, as well as providing levomilnacipran with excellent yields and purity, offers the advantage of a simple and complete recovery of the resolving agent from the reaction mother liquors. Moreover, with respect to known methods, it also offers the advantage of using cheap raw materials. In particular, costs of the resolving agents of the process of the invention are significantly lower than those of tartaric acid derivatives. In addition, with respect to synthetic pathways that consider the use of a derivative of tartaric or mandelic acid, the process of the invention allows to obtain excellent yields, greater than 90%, generally around 93-95%, and an optical purity of 100% already at the first crystallization step. Comparative tests carried out by the applicant, by using mandelic acid, provided significantly poor results with yields of about 70%.

As said, the resolving agent can be easily recovered. As a matter of fact, the recovery of N-Boc-L-(+)-phenylglycine from mother liquors can be done by completely evaporating the solvent and taking-up the obtained mixture with H₂O/DCM, then adding 10% sodium hydroxide up to basic pH. The aqueous phase is then treated with 2N HCL and followed by extraction with DCM; the remaining N-Boc-L-(+)-phenylglycine is thus recovered which, together with the recovery from the crystallized salt, provides a global recovery yield greater than 90%.

The separation of enantiomers of cis-milnacipran by means of resolution with an optically active phenylglycine derivative can be also carried out by using N-protected D-(−)-N-phenylglycine, for example the N-Boc-D-(−)-phenylglycine, and thus obtaining the precipitation of the (1R, 2S)-cis-milnacipran D-(−)-N-Boc-phenylglycinate. In this case, levomilnacipran, i.e. the desired enantiomer, can be recovered from the mother liquors.

EXPERIMENTAL SECTION

Example 1

Preparation of Racemic Cis-Milnacipran Free Base

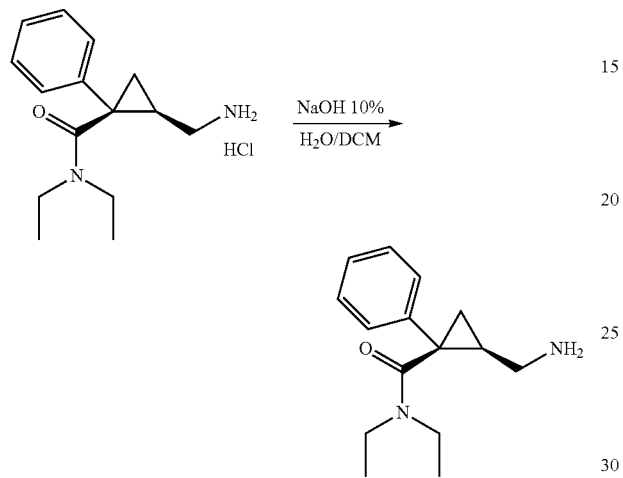

10 g (35.44 mmol) of racemic cis-milnacipran hydrochloride have been suspended in a mixture of 50 ml water and 100 ml dichloromethane. A solution of 10% sodium hydroxide (15 ml) is added to the mixture and stirring is carried out at room temperature up to pH=11. The organic phase is separated, the aqueous phase is extracted three times with dichloromethane (60 ml each time) and the organic phases are combined. They are dried on anhydrous sodium sulphate and filtered. The solvent is evaporated under reduced pressure and 8.7 g (35.34 mmol, quantitative yield) of racemic cis-milnacipran free base are obtained.

MS (ESI$^+$): 247.2 (M+H$^+$), 493.4 (2M+H$^+$).

Example 2

Preparation of N-Boc-Phenylglycine

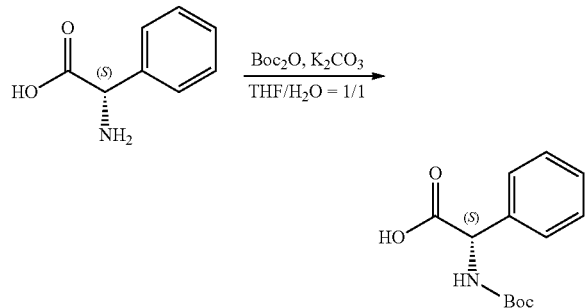

Phenylglycine (5.1 g, 33.76 mmol) is suspended in a 1:1 mixture of water and THF (50 ml) at room temperature and potassium carbonate (K$_2$CO$_3$, 11.66 g, 84.4 mmol) and Boc anhydride (7.36 g, 84.4 mmol) are added. The suspension is stirred at room temperature for 18 hours, controlling by LC-MS. The solids are removed by filtration and THF is evaporated under reduced pressure. The remaining aqueous phase is acidified with a 2N HCl aqueous solution and extracted two times with dichloromethane (40 ml each time). The organic phases are combined and dried on sodium sulphate. The suspension is filtered and the solvent is evaporated under reduced pressure. Petroleum ether is added during the evaporation to facilitate the precipitation. A white solid is obtained, which is filtered and dried to give 8.02 g of the title product (31.91 mmol; yield 95%).

MS (ESI$^+$): 252.2 (M+H$^+$), 525.3 (2M+Na)

$^1$H-NMR (400 MHz, DMSO): 12.75 (s, 1H, —OH), 7.55 (d, 11, —NH-Boc, J=8.4 Hz) 7.41-7.33 (m, 5H, Ph), 5.11 (d, 1H, Hα, J=8.4 Hz), 1.39 (s, 9H, 3× —CH$_3$).

Example 3

Preparation of the Salt Between Levomilnacipran and N-Boc-L-(+)-Phenylglycine

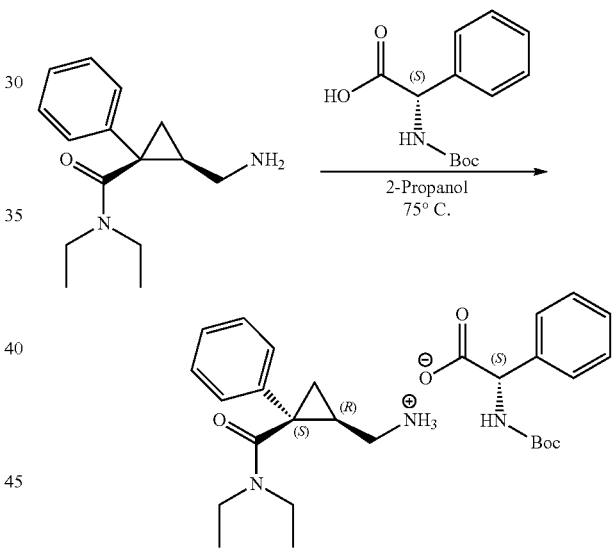

Racemic cis-milnacipran free base (34.7 g, 141.03 mmol) is dissolved in 175 ml of 2-propanol and heated to 65° C. A solution of N-Boc-L-(+)-phenylglycine (35.4 g 141.03 mmol) in 2-propanol (175 ml) is then added dropwise under vigorous stirring. The mixture is heated to 75° C. until a clear solution is obtained which is slowly cooled to room temperature, possibly with seeding with a crystal around 65° C. The mixture is then cooled to 0-5° C. and filtered. The filtered solid is washed two times with cold 2-propanol (100 ml total) and dried to give 31.5 g of (1S,2R)-cis-milnacipran salt of N-Boc-L-(+)-phenylglycine (65.31 mmol, yield 93%).

The mother liquors are worked-up for the full recovery of N-Boc-L-(+)-phenylglycine.

MS (ESI$^+$): Milnacipran 247.2 (M+H$^+$), 493.4 (2M+H$^+$); N-Boc-L-(+)-phenylglycine 252.2 (M+H$^+$), 525.3 (2M+Na)

Chiral-HPLC: 100% e.e.

Example 4

Preparation of Levomilnacipran Free Base ((1S,2R)-cis-2-(aminomethyl)-N,N-diethyl-1-phenylcyclopropanecarboxamide)

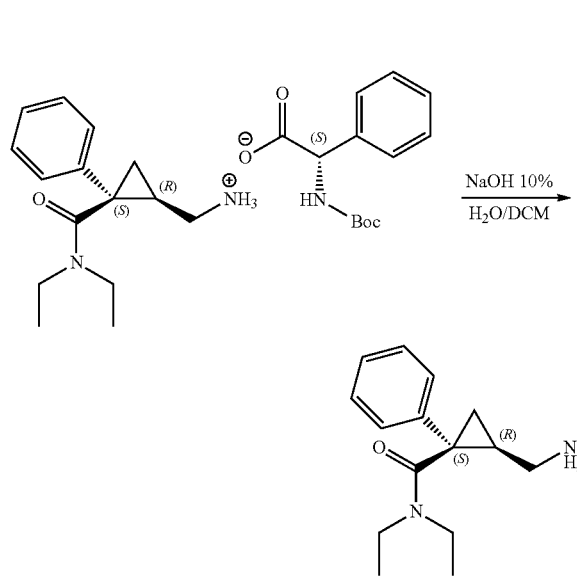

The salt obtained in Example 3 is suspended in water (250 ml), 25 ml of 10% sodium hydroxide solution are added and stirred at room temperature up to pH=11. Dichloromethane (250 ml total) is added under vigorous stirring and the mixture is stirred for 5 minutes. The organic phase is separated, the aqueous phase is extracted three times with dichloromethane (250 ml) and the organic phases are combined. They are dried on anhydrous sodium sulphate and the suspension is filtered. The solvent is evaporated under reduced pressure and 15.8 g (63.9 mmol, quantitative yield) of the title compound are obtained.

The aqueous phase was acidified with 2N HCl up to pH=2 and extracted 2 times with dichloromethane (150 ml each time), the combined organic phases are dried on sodium sulphate and the solvent evaporated, 15.9 (g) of N-Boc-L-(+)-phenylglycine are obtained (first recovery).

MS (ESI+): Milnacipran 247.2 (M+H+), 493.4 (2M+H+); N-Boc-L-(+)-phenylglycine 252.2 (M+H+), 525.3 (2M+Na)

Example 5

Preparation and Purification of Levomilnacipran Hydrochloride

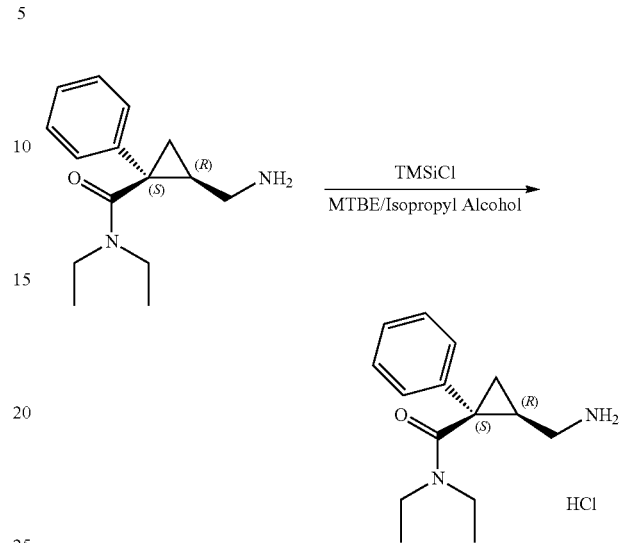

Trimethyl silyl chloride (9.7 ml, 76.7 mmol) is added dropwise to a solution of the compound of Example 4 (15.7 g, 63.9 mmol) in methyl-tert-butyl ether (150 ml) and 2-propanol (25 ml), and the formation of a white solid occurs. The mixture is stirred for 30 minutes, cooled to 20° C. and filtered. The filtered solid is washed with 35 ml of cold methyl-tert-butyl ether and dried under vacuum for 20 hours. 17.2 g of levomilnacipran hydrochloride (60.81 mmol, yield 95%) are obtained.

2-propanol (44 ml) is added to the obtained product (17.2 g, 60.81 mmol) and it is heated to 75° C. until complete dissolution, cooled to RT and the formation of a white solid occurs. It is filtered and washed with cold 2-propanol (6 ml), and 13.5 (g) of the product are obtained.

50 ml of methyl-tert-butyl ether are added to the mother liquors and it is stirred at room temperature for 30 minutes, then left to decant, filtered and washed with cold methyl-tert-butyl ether. 2.72 (g) of the product are obtained, that combined with the previous one gives an overall yield of 89.6%.

Example 6

Recovery of N-Boc-L-(+)-Phenylglycine

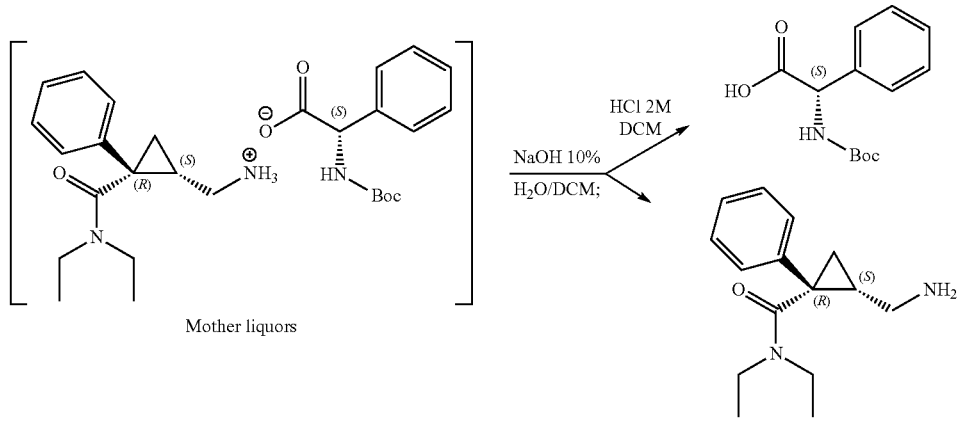

The solvent is completely evaporated from, the mother liquors obtained from the filtration, of Example 3, containing the (1R,2S)-cis-milnacipran enantiomer and the N-Boc-L-(+)-phenylglycine, the residue is taken-up with water (250 ml) and a 10% sodium hydroxide solution is added up to pH=11. Under vigorous stirring dichloromethane (250 ml) is added and stirred for about 5 minutes. The phases are separated and the aqueous phase is further extracted with dichloromethane (150 ml for 2 times). Once the organic phases are combined and dried the solvent is evaporated, and 16.2 (g) of (1R,2S)-cis-milnacipran are obtained as a yellow oil.

The aqueous phase is acidified with 2N HCl up to pH=2 and extracted 2 times with dichloromethane (150 ml each time), the combined organic phases are dried on sodium sulphate and the solvent is evaporated, 16.9 (g) of N-Boc-L-(+)-phenylglycine are obtained (second recovery).

Totally recovered N-Boc-L-(+)-phenylglycine is 32.8 (g), with a yield of 93% based on the amount used in the whole process.

MS (ESI$^+$): Milnacipran 247.2 (M+H$^+$), 493.4 (2M+H); N-Boc-L-(+)-phenylglycine 252.2 (M+H$^+$), 525.3 (2M+Na)

The invention claimed is:

1. A process for preparing levomilnacipran ((1S,2R)-cis-milnacipran) of formula (I)

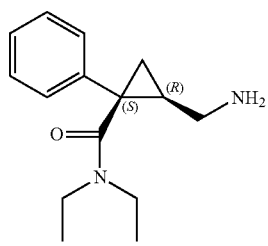

(I)

or a salt thereof, comprising resolution of cis-milnacipran with optically active phenylglycine or optically active N-Boc-phenylglycine.

2. A process for preparing levomilnacipran ((1S,2R)-cis-milnacipran) of formula (I) or salts thereof, comprising
   (a) reacting racemic cis-milnacipran free base with an the optically active L-phenylglycine of formula (II)

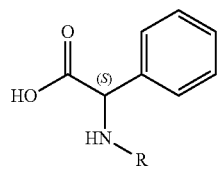

(II)

wherein R is an amine protecting group selected from tert-butyloxycarbonyl (Boc), benzoyl and p-methoxybenzylcarbonyl, in a non-aqueous organic solvent, to give the salt of formula (III)

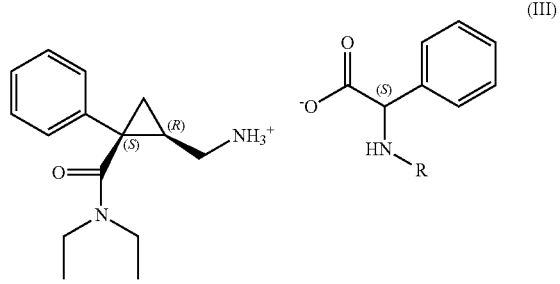

(III)

(b) reacting the salt of formula (III) obtained in step (b) with a base, in water, to release levomilnacipran of formula (I);
   (c) isolating said levomilnacipran from the reaction mixture of step (b) and optionally purifying it and/or transforming it into a salt of said levomilnacipran.

3. The process according to claim 2, wherein R is a BOC (tert-butyloxycarbonyl) group.

4. The process according to claim 2, wherein said non-aqueous organic solvent is selected from alcohols, ketones and esters.

5. The process according to claim 4, wherein said non-aqueous organic solvent is an alcohol.

6. The process according to claim 5, wherein said alcohol is 2-propanol.

7. The process according to claim 2,
wherein step (a) is performed at a temperature from 60° C. to 80° C.

8. The process according to claim 2, wherein a molar ratio of racemic cis-milnacipran to the compound of formula (II) is essentially equimolar.

9. The process according to claim 2, wherein in step (c) levomilnacipran is transformed into levomilnacipran hydrochloride.

10. A compound of formula (III)

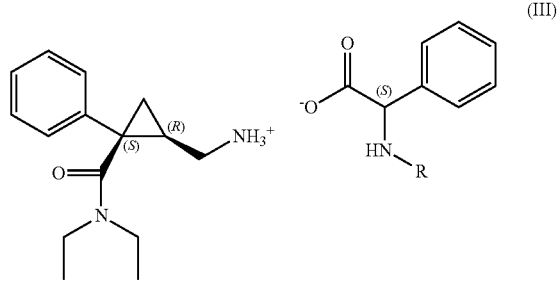

(III)

wherein R is an amine protecting group.

11. The compound according to claim 10 having the formula (III')

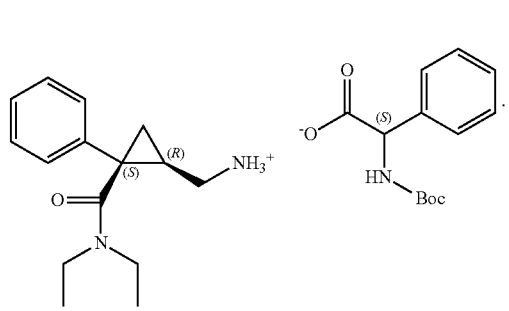
(III′)
\* \* \* \* \*